(12) United States Patent
Geng et al.

(10) Patent No.: US 9,493,496 B2
(45) Date of Patent: *Nov. 15, 2016

(54) ALGIN OLIGOSACCHARIDES AND THE DERIVATIVES THEREOF AS WELL AS THE MANUFACTURE AND THE USE OF THE SAME

(71) Applicant: Ocean University Of China, Qingdao, Shandong Province (CN)

(72) Inventors: Meiyu Geng, Qingdao (CN); Huashi Guan, Qingdao (CN); Xianliang Xin, Qingdao (CN); Zhao Yang, Qingdao (CN); Guangqiang Sun, Qingdao (CN)

(73) Assignee: Ocean University Of China, Qingdao (CN)

( * ) Notice: Subject to any disclaimer, the term of this patent is extended or adjusted under 35 U.S.C. 154(b) by 0 days.

This patent is subject to a terminal disclaimer.

(21) Appl. No.: 14/482,610

(22) Filed: Sep. 10, 2014

(65) Prior Publication Data

US 2015/0105344 A1     Apr. 16, 2015

Related U.S. Application Data

(63) Continuation of application No. 10/594,100, filed as application No. PCT/CN2005/000226 on Feb. 25, 2005, now Pat. No. 8,835,403.

(30) Foreign Application Priority Data

Mar. 24, 2004 (CN) .......................... 2004 1 0023827

(51) Int. Cl.
| | | |
|---|---|---|
| *C07H 3/04* | (2006.01) | |
| *C08B 37/04* | (2006.01) | |
| *A61K 31/734* | (2006.01) | |
| *C07H 3/06* | (2006.01) | |
| *C08B 37/00* | (2006.01) | |

(52) U.S. Cl.
CPC ........ *C07H 3/06* (2013.01); *C07H 3/04* (2013.01); *C08B 37/0024* (2013.01); *C08B 37/0084* (2013.01)

(58) Field of Classification Search
None
See application file for complete search history.

(56) References Cited

U.S. PATENT DOCUMENTS

| | | | |
|---|---|---|---|
| 5,460,945 A | 10/1995 | Springer et al. | |
| 5,516,666 A | 5/1996 | Nozomi et al. | |
| 5,952,308 A * | 9/1999 | Nakanishi ............. | C07H 3/06 514/25 |
| 6,436,389 B1 | 8/2002 | Gage et al. | |
| 8,835,403 B2 | 9/2014 | Geng | |
| 2002/0016453 A1 | 2/2002 | Marritt | |

FOREIGN PATENT DOCUMENTS

| | | |
|---|---|---|
| CN | 1341664 A | 3/2002 |
| CN | 1341665 A | 3/2002 |
| CN | 1380342 A | 11/2002 |
| CN | 1401786 A | 3/2003 |
| CN | 1408360 A | 4/2003 |
| CN | 1414002 A | 4/2003 |
| CN | 1454992 A | 11/2003 |
| CN | 1473836 A | 2/2004 |
| CN | 1486988 A | 4/2004 |
| CN | 1562050 A | 1/2005 |
| JP | 2002-047302 A | 2/2002 |
| JP | 2003-521573 A | 7/2003 |
| WO | WO-01/56404 A1 | 8/2001 |
| WO | WO 03/099870 | * 12/2003 |

OTHER PUBLICATIONS

Ariyo, B. et al "Enhanced penicillin production by oligosaccharides . . . " FEMS Lett. (1998) vol. 166, pp. 165-170.*
Machine translation of Brault et al WO 03/099870 (2003).*
Rehm, B. "Alginate lyase from Pseudomonas aeruginosa . . . " FEMS Microbiol. Lett. (1998) vol. 165, pp. 175-180.*
Biessels GJ, et al., Risk of dementia in diabetes mellitus: a systematic review. Lancet Neurol. Jan. 2006;5(1):64-74.
Clark, A., et al., Pancreatic islet amyloid and diabetes, Protein Reviews (2007) vol. 7, part 3, pp. 1199-1216.
Davies MJ, et al., Prevention of Type 2 diabetes mellitus. A review of the evidence and its application in a UK setting. Diabet Med. May 2004;21(5):403-14.
De Haas et al., A synthetic lipopolysaccharide-binding peptide based on amino acids 27-39 of serum amyloid P component inhibits lipopolysaccharide-induced responses in human blood, J. Immunol., 1998, vol. 161, pp. 3607-3615.

(Continued)

*Primary Examiner* — Leigh C Maier

(74) *Attorney, Agent, or Firm* — McCarter & English, LLP; Steven G. Davis; Wei Song

(57) ABSTRACT

The invention provides an alginate oligosaccharide and its derivatives with the degree of polymerization ranging from 2 to 22. The alginate oligosaccharide is composed of β-D-mannuronic acid linked by 1,4 glycosidic bonds. The derivatives with the reduced terminal in position 1 of carboxyl radical can be prepared by oxidative degradation. The invention also provides a process for preparing the alginate oligosaccharide and its derivatives, which includes the procedure that an alginate solution is reacted for 2 to 6 h in an autoclave at pH 2~6 and the temperature of 100~120° C., and adjusted pH to 7 after the reaction is stopped, after which the resultant oligosaccharide is oxidized in the presence of an oxidant to obtain an oxidative product. The alginate oligosaccharide and its derivatives of the invention can be used in the manufacture of a medicament for the prophylaxis and treatment of AD and diabetes.

4 Claims, 9 Drawing Sheets

(56) References Cited

OTHER PUBLICATIONS

Doraiswamy PM, et al., Pharmacological strategies for the prevention of Alzheimer's disease. Expert Opin Pharmacother. Jan. 2006;7(1):1-10.

Hamilton J, et al., Metformin as an adjunct therapy in adolescents with type 1 diabetes and insulin resistance: a randomized controlled trial. Diabetes Care. Jan. 2003;26(1):138-43.

International Search Report for International Application No. PCT/CN20051000226 dated May 19, 2005.

Leca et al., Expression of VCAM-1 (CD106) by a subset of TCRγδ-bearing lymphocyte clones, J. Immunol., 1995, vol. 154, pp. 1069-1077.

Machine Translation of CN 1408360 (2003).

Marchesi VT. Alzheimer's dementia begins as a disease of small blood vessels, damaged by oxidative-induced inflammation and dysregulated amyloid metabolism: implications for early detection and therapy. FASEB J. Jan. 2011;25(1):5-13.

MESH definition of "oligosaccharide" retrieved May 21, 2012 http://www.nlm.nih.gov/cgi/mesh/2012/MB_cgi?mode=&index=9431&field=all&HM=&11=&PA=&form=&input=.

Rogers et al., Epitope mapping of the Syrian hamster prion protein utilizing chimeric and mutant genes in a vaccinia virus expression system, J. Immunol., 1991, vol. 147, pp. 3568-3574.

Skyler JS, et al., Effects of oral insulin in relatives of patients with type 1 diabetes: The Diabetes Prevention Trial—Type 1. Diabetes Care. May 2005;28(5):1068-76.

Translation of Chinese application CN 01107952.5 (2002).

Yang Z, et al., Preparation and characterization of oligomannuronates from alginate degraded by hydrogen peroxide, Carbohydrate Polymers, 2004, 58(2):115-121.

* cited by examiner

ALGIN OLIGOSACCHARIDES AND THE DERIVATIVES THEREOF AS WELL AS THE MANUFACTURE AND THE USE OF THE SAME

TECHNICAL FIELD

The invention relates to an alginate oligosaccharide and its derivatives, the preparation thereof, and uses of the same for treating Alzheimer's disease (AD) and diabetes.

BACKGROUND ART

Alzheimer's disease (AD) and diabetes are currently common and frequently-occurring disease. Especially, their incidence is increasing as the old people growing. So the prevention and cure of these diseases are urgent problems to be solved today.

Current drugs therapy for AD are unlikely to revolutionize the treatment of AD due to their limitation of the mere symptomatic relief or severe adverse effects. The current drugs used for diabetes mainly are insulin and other orally hypoglycemic drugs. The inconveniency for long-term use and toxicity limited their wide applications and there are actually no effective drugs for type 2 diabetes. The recent study revealed that amyloid-beta (A β) and amylin (IAAP) are the basic molecules of AD and type 2 diabetes. The fibrillogenesis and subsequently increased free oxidative radicals are the triggers of these diseases, which gives rise to the fact that the fibril formation inhibitor of amyloid-beta and amylin becomes the perspective for the cure of these diseases.

Alginates are a family of linear polysaccharide produced by brown seaweeds and some bacterial species belonging to the genera *Pseudomonas* and *Azotobacter*. These polymers are composed of two hexuronic acids, β-D-mannuronic acid (ManA) and α-L-guluronic acid (GulA), linked by 1-4 bonds. Alginate belongs to high polymers with molecular weight of several $10^4$ to $10^6$ with very abundant source. The polymer alginate has been used for a variety of industrial purposes, e.g. as a stabilizing, thickening and gelling agent in food production and pharmaceutical applications. Recent developments revealed that alginate is an important biological active compound. Its application as a drug is largely limited by its huge molecular weight. So the oligosaccharide degraded from alginate by different methods is very valuable for glycochemistry, glycobiology, glycoengineering and saccharide-based drugs. The currently-used methods to degrade alginate include enzymatic, physical and chemical treatments, yet the finding of specific lyases has limited the application by enzymatic method. Physical method, which is usually used in combination with other method, couldn't get oligosaccharide with the minimal molecular weight of 50,000. The chemical degraded method used for polysaccharides include acidic hydrolysis method and hydrogen peroxide degraded method. The former method is limited by its capacity to get oligosaccharides with weight less than 4000 when conducted in normal temperature and pressure.

Contents of the Invention

Through deep studies by the inventors, it is found that an alginate oligosaccharide with molecular weight below 4000 can be obtained by acid hydrolysis at high temperature and pressure, and its derivatives whose reduced terminal in position 1 is carboxyl radical can be prepared in the presence of oxidants. The invention is completed on the above basis.

The invention provides an alginate oligosaccharide and its derivatives with low molecular weight, or pharmaceutically-acceptable salts thereof, and provides the process for preparing the same. The invention also provides a medicament for the prophylaxis and treatment of AD and diabetes with the above-mentioned low molecular alginate oligosaccharide or its derivatives, or pharmaceutically-acceptable salts thereof.

The invention relates to an alginate oligosaccharide and its derivatives represented by formula (I) or pharmaceutically-acceptable salts thereof, the above-mentioned oligosaccharide is composed of β-D-mannuronic acid linked by 1,4 glycosidic bonds,

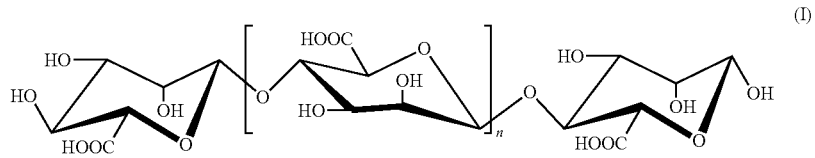

(I)

wherein, n represents an integer of 0 or any number ranging from 1 to 19.

In the present invention, an example of the above alginate oligosaccharide derivatives is a compound represented by formula (II), in which the reduced terminal in position 1 is carboxyl radical,

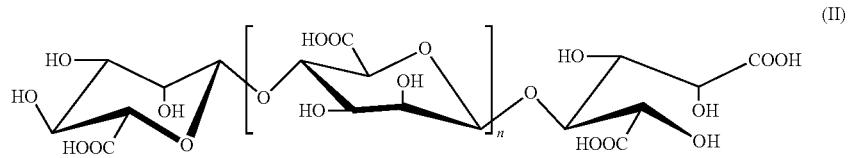

(II)

wherein, n represents a integer of 0 or 1 to 19.

In above formula (I) and (II), preferable n is 2 to 10, and more preferable n is 4 to 8. The reason why better biological effects of tetrasaccharide over dodecasaccharide (preferably, hexasaccharide to decasaccharide) remains unclear, which may be caused by its liability to be recognized and accepted by cells.

The alginate oligosaccharide derivatives also include, for example, the derivatives, of which part of the hydroxyl groups in mannuronic acid are sulfated.

For example, the pharmaceutically-acceptable salts of the above alginate oligosaccharide and its derivatives can be salts of sodium, potassium, calcium, magnesium salts and the like. The sodium salts are preferred. The pharmaceutically-acceptable salts can be prepared by the conventional methods.

The invention also relates to a process for preparing above alginate oligosaccharide and its derivatives, characterized by the fact that an alginate solution is reacted for about 2 to 6 h in an autoclave at pH 2~6 and the temperature of about 100~120° C.; after which the value of pH is adjusted to about 7. The oxidative product is obtained by the addition of an oxidant to the alginate oligosaccharide solution.

In a preferred embodiment of the invention, a 0.5~5% sodium alginate solution is heated to 110° C. for 4 h in an autoclave at pH 4. After the reaction is accomplished, the reactant is sucked out and cooled, then pH is adjusted to 7 by adding NaOH solution. With stirring, the filtrate is slowly poured in to industrial alcohol which is 4 times as the volume of the filtrate, and stayed overnight to allow precipitation. The alcohol precipitate is filtered off with suction to dryness, and is dehydrated by washing with absolute ethanol. A white filter cake is obtained and dried in an oven at 60° C. to give a crude alginate oligosaccharide. The crude alginate oligosaccharide is formulated to a 10% solution, and is precipitated with 95% ethanol solution. The precipitate washed with absolute ethanol, dried and formulated to a 5% solution. The solution is filtered through a 3 μm membrane to remove impurity, then desalted on a Bio-Gel-P6 column (1.6×180 cm) with 0.2 mol/L $NH_4HCO_3$ as mobile phase and then the product is obtained collected. The elute is detected by the sulfate-carbazole method, collected components including sugar, concentrated under reduced pressure and desalted, and lyophilized to give the alginate oligosaccharide.

The preparations of the derivatives represented by formula (II) is are as follows: an oxidant is added and reacted for 15 min to 2 h at the temperature of 100~120° C. after the step when the above alginate solution reacting for about 2 to 6 h in an autoclave at pH 2~6 and the temperature of about 100~120° C. In an embodiment of the invention, 25 ml of 5% copper sulfate is added to 50 ml of 10% NaOH (aq), mixed immediately, and immediately added 40 ml of 5% alginate oligosaccharide solution. The resultant mixture is heated in a boiling water bath until no more brick red precipitate is generated. The mixture is centrifuged to remove precipitate. Some supernatant is taken out and added to 10% NaOH (aq) and 5% copper sulfate according to the above ratio to check any generation of brick red precipitate. If negative, the supernatant is added to industrial alcohol which is 4 times the volume to of the supernatant, and stayed overnight to allow precipitation. The precipitate is filtered off with suction to dryness, dehydrated with absolute ethanol repeatedly and dried in an oven at 60° C. The separation is preceded according to the same separation method of the alginate oligosaccharide of formula (I).

The invention also provides a pharmaceutical composition containing an effective amount of such alginate oligosaccharide or its derivatives, or pharmaceutically-acceptable salts thereof and pharmaceutically-acceptable carriers.

The pharmaceutical composition can be a medicament for the prophylaxis and treatment of AD.

Furthermore, the pharmaceutical composition can be an amyloid-β protein fibrils forming inhibitor and fibrils disaggregating promoter.

The pharmaceutical composition also can be a medicament for the prophylaxis and treatment of diabetes.

Moreover, the pharmaceutical composition can be used as pancreatic islet amyloid protein fibrils forming inhibitor and islet amyloid polypeptide inhibitor. In view of the current difficulty of lacking effective medicines for the prophylaxis and treatment of AD and diabetes, it is especially important that the alginate oligosaccharide of the invention is used in the manufacture of a medicament for the prophylaxis and treatment of AD and diabetes.

EMBODIMENTS

1 Preparation of the Alginate Oligosaccharide

One gram of sodium polymannanuronate (average molecular weight of 8,235 Da, provided by Lantai Pharm.

LTD., Ocean University of China) is added to distilled water to obtain a 1% solution, adjusted pH to 4 with HCl, placed into an autoclave and heated at 110° C. for 4 h. After cooling, the solution of pH is adjusted to 7 with NaOH (aq.). With stirring, the filtrate is slowly poured into industrial alcohol which is 4 times the volume of the filtrate, and stayed overnight to precipitate. The alcohol precipitate is filtered off with suction to dryness, and is dehydrated by washing with absolute ethanol. A white filter cake is obtained and dried in an oven at 60° C. to give a crude alginate oligosaccharide.

Figure 1:
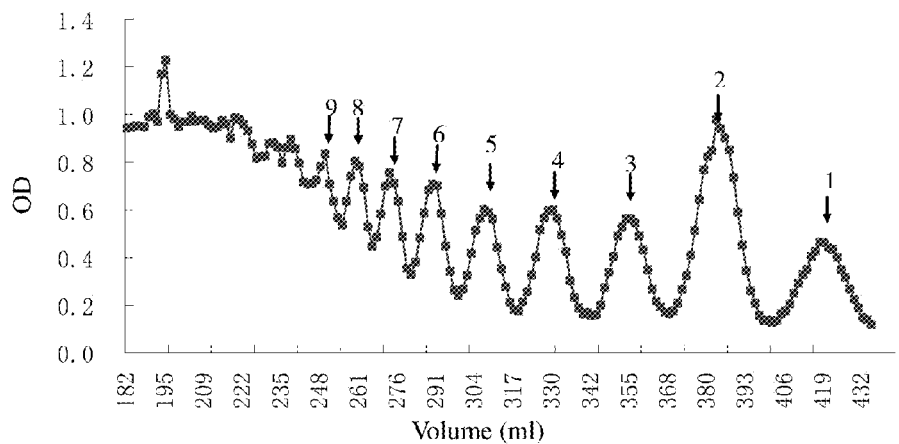
FIG. 1 shows the eluting curve of the alginate oligosaccharide according to the invention separated by a Bio-Gel-P6 column after acid hydrolysis.

The crude alginate oligosaccharide is formulated to a 10% solution, and is precipitated with 95% ethanol solution. The precipitate is washed with absolute ethanol, after drying, formulated to a 5% solution. The solution is filter through a 3 μm membrane to remove impurity, then desalted on a Bio-Gel-P6 column (1.6×180 cm) with 0.2 mol/L $NH_4HCO_3$ as mobile phase and collected. The elute is detected by the sulfate-carbazole method, collected components including sugar, concentrated under reduced pressure and desalted on G-10 column. The outer volume component is further separated by a Bio-Gel-P10 column and lyophilized to give a series of alginate oligosaccharide (FIG. 1).

2 Preparation of the Oxidative Product of the Alginate Oligosaccharide

Five gram of above prepared alginate oligosaccharide is formulated to a 5% solution. 25 ml of 5% copper sulfate is added to 50 ml of 10% NaOH (aq), and mixed immediately, then add 40 ml solution of 5% alginate oligosaccharide. The resultant mixture is heated in a boiling water bath until no more brick red precipitate is generated. The mixture is centrifuged to remove precipitate. A few of supernatant is taken out and added to 10% NaOH (aq) and 5% copper sulfate according to the above ratio to check for brick red precipitate. If negative, the supernatant is added to industrial alcohol which is 4 times the volume of the supernatant, and stayed overnight to allow precipitation. The precipitate is filtered off with suction to dryness, dehydrated with absolute ethanol repeatedly and dried in an oven at 60° C. Thus a crude oxidative product of alginate oligosaccharide is obtained.

Figure 2:
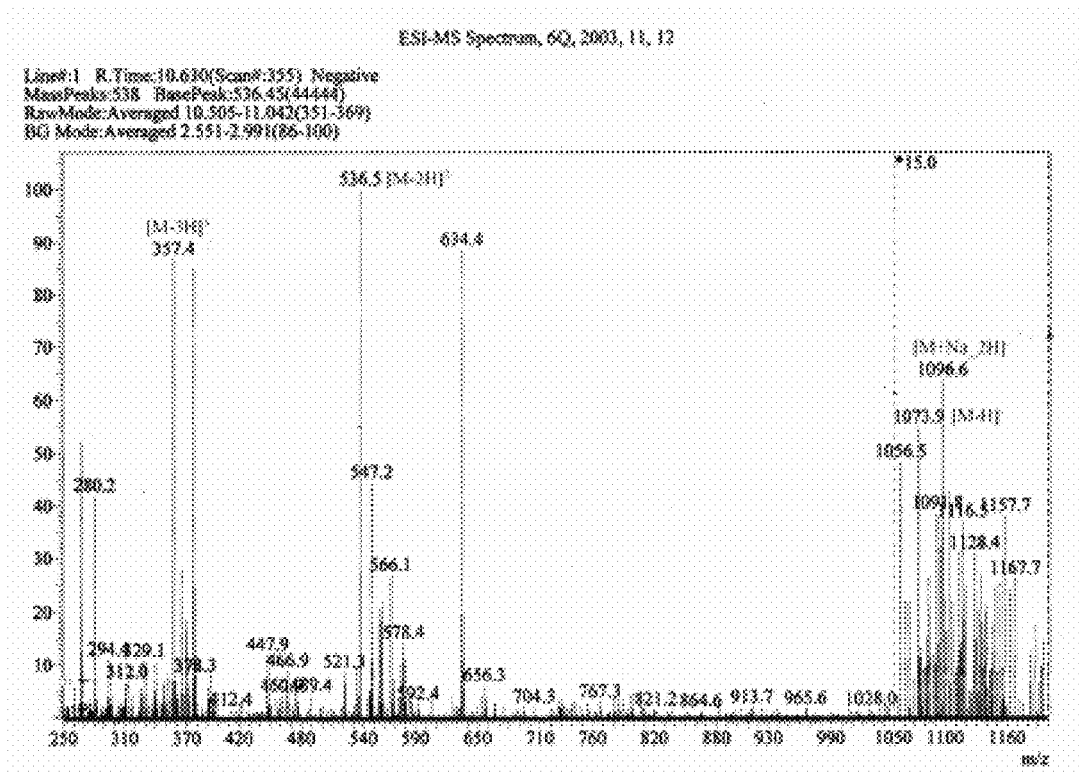
FIG. 2 shows the MALDI-TOF spectrum of the alginate oligosaccharide according to the invention.
Figure 3:
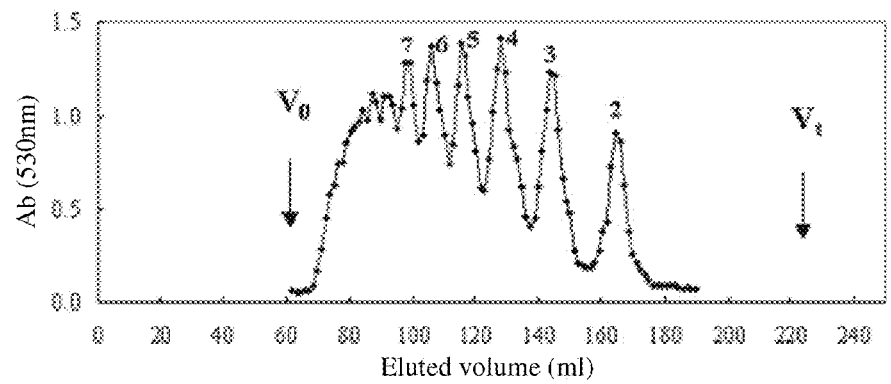
FIG. 3 shows the eluting curve of the oxidative product of the alginate oligosaccharide separated by a Bio-Gel-P6 column.

The crude oxidative product of alginate oligosaccharide is formulated to a 10% solution, and is precipitated with 95% ethanol solution. The precipitate is washed with absolute ethanol, after drying, formulated to a 5% solution. The solution is filter through a 3 μm membrane to remove impurity, then desalted on a Bio-Gel-P6 column (1.6×180 cm) with 0.2 mol/L $NH_4HCO_3$ as mobile phase and collected. The elute is detected by the sulfate-carbazole method, collected components including sugar, concentrated under reduced pressure and desalted on G-10 column. The outer volume component is further separated by a Bio-Gel-P10 column and lyophilized to give a series of oxidative product (FIG. 2).

3 Structure Identification of the Alginate Oligosaccharide

The structure of oligosaccharide fraction obtained from the preparation of the alginate oligosaccharide is identified. The oligosaccharide is confirmed to be an alginate oligosaccharide composed of β-D-mannuronic acid linked by 1,4 glycosidic bonds. The structural formula is:

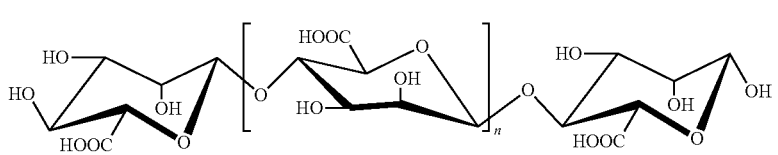

(I)

wherein, n represents an integer of 0 or any from 1 to 19.

The fraction at about 292 ml of the elute (the fraction labeled as "6" in FIG. 1, hereinafter referred to as Component 6) is taken as an example to illustrate the structure analysis of above oligosaccharide.

3.1 Ultraviolet Absorption Spectrogram

The oligosaccharide fraction at about 292 ml of the elute is diluted to an appropriate concentration, and scanned at 190 nm~400 nm with UV-2102 UV-VIS spectrophotometer. It is found that no specific absorption peak appeared in ultraviolet region, indicating that the structure is void of conjugated double bond. However, non-specific absorption peak appeared at 190~200 nm Thus, during desalting the oligosaccharide, it can be on-line detected at above ultraviolet region.

3.2 Infrared Spectroscopy Analysis

Five hundred microgram of above oligosaccharide fraction is weighed. Infrared spectroscopy is determined with NEXUS-470 intelligent infrared spectrometer by KBr pellet. The peaks at 3420.79, 3214.64, and 2924.61 $cm^{-1}$ are attributable to symmetry stretching vibrations of hydroxyl group; the peak at 1600.25 $cm^{-1}$ is attributable to symmetry stretching vibration of carbonyl of carboxylate; the peak at 1406.54 $cm^{-1}$ is attributable to shearing vibration of hydroxyl group; the peak at 1146.42 $cm^{-1}$ is attributable to symmetry stretching vibration of C—O bond of carboxyl; the peak at 1045.77 $cm^{-1}$ is attributable to anti-symmetry stretching vibrations of anhydro ether; and the peak at 804.02 $cm^{-1}$ is attributable to anti-symmetry stretching vibrations of mannuronic acid cyclic skeleton. It is demonstrated that such compound has carboxyl, hydroxyl and mannuronic acid cyclic skeleton.

3.3 MS Analysis

MS analysis is performed with BIFLEX II type MALDI-TOF mass spectrometer (Bruker Daltonics Co.). As seen from FIG. 2, the peak of mz 1073.9 is the molecular ion peak $[M-H]^{-1}$; mz 1096.6 is $[M+Na-2H]^{-1}$; mz 1028.0 is $[M-H2O-CO-H]^{-1}$; mz 821.2 is $[M-ManA-CH2O-2H2O-H]^{-1}$; mz 704.3 is $[M-2ManA-H2O-H]^{-1}$; mz 634.4 is $[M-2ManA-2(CH2O)-CO-H]^{-1}$; mz 536.5 is $[M-2H]^{2-}$; and mz 357.4 is $[M-3H]^{3-}$. In ESI-MS spectrum of above oligosaccharide fraction, the molecular ion peak is mz 1073.9, indicating that molecular weight is 1074.

TABLE 1

MS analysis of the alginate oligosaccharide (Component 6)

| Fragment ions | m/z |
|---|---|
| $[M - H]^{-1}$ | 1073.9 |
| $[M + Na—2H]^{-1}$ | 1096.6 |
| $[M - H_2O—CO—H]^{-1}$ | 1028.0 |
| $[M-ManA-CH_2O—2H_2O—H]^{-1}$ | 821.1 |
| $[M-2ManA-H_2O—H]^{-1}$ | 704.3 |
| $[M-2ManA-2(CH_2O)—CO—H]^{-1}$ | 634.4 |
| $[M - 2H]^{2-}$ | 536.5 |
| $[M - 3H]^{3-}$ | 357.4 |

3.4 Nuclear Magnetic Resonance Spectroscopy of the Alginate Oligosaccharide $^1$H NMR and $^{13}$C NMR of the alginate oligosaccharide represented by formula (I) (n=4) are obtained by JNM-ECP600 NMR spectrometer. The results are shown in table 2 and 3.

TABLE 2

$^1$H-NMR of the alginate oligosaccharide (Component 6)

| | Chemical shift (ppm) | | | | |
|---|---|---|---|---|---|
| | H-1 | H-2 | H-3 | H-4 | H-5 |
| r α | 5.21 | 3.98 | 4.03 | 4.04 | 4.16 |
| r β | 4.91 | 3.99 | 3.77 | 3.90 | 3.77 |
| m α | 4.69 | 4.03 | 3.75 | 3.93 | 3.69 |
| m β | 4.64 | 4.03 | 3.75 | 3.65 | 3.69 |
| n | 4.63 | 3.74 | 3.63 | 3.75 | 4.01 |

TABLE 3

$^{13}$C-NMR of the alginate oligosaccharide (Component 6)

| | Chemical shift (ppm) | | | | | |
|---|---|---|---|---|---|---|
| | C-1 | C-2 | C-3 | C-4 | C-5 | C-6 |
| r α | 93.54 | 70.06 | 69.02 | 78.37 | 72.60 | 175.84 |
| r β | 93.74 | 70.42 | 71.60 | 78.28 | 76.08 | 175.84 |
| m | 99.08 | 70.63 | 71.43 | 78.07 | 75.90 | 175.41 |
| n | 100.15 | 68.48 | 72.47 | 76.27 | 70.05 | 175.27 |

According to above analysis results, it is confirmed that the alginate oligosaccharide in above fraction is mannuronic hexasaccharide with the following structure (Ia):

3.5 Determination of the Content of Mannuronic Acid in the Alginate Oligosaccharide ($^1$H-NMR Spectroscopy)

Constitute of the alginate oligosaccharide is determined by high resolution $^1$H-NMR to quantify the ratio of mannuronic acid to guluronic acid (MG) in the alginate oligosaccharide according to the signal intensity of proton of anomeric carbon. Three to five mg of dried sample is weighed and dissolved in $D_2O$ at neutral pD. Three hundred microgram of EDTA is added. The sample is determined by Bruker DPX-300 NMR spectrometer. The spectrum is reported at 70° C., making the peak of $D_2O$ far away from anomeric proton resonance region. The signal relative intensity is expressed by the integral of the peak area. The results shown that H-1 signals of M radical appeared at 4.64 ppm and 4.66 ppm (i.e. H-1 signals of M radical in MM and MG sequence respectively); all of H-1 signals of G radical appeared at 5.05 ppm (double peak). The relative content of M and G in the sample can be expressed by their H-1 peak intensity, as the following equation:

$$M\% = \frac{I_{4.64} + I_{4.66}}{I_{4.64} + I_{4.66} + I_{5.05}} \times 100\%$$

wherein, I represents the peak intensity, expressed by the integral of the peak area.

The relative content of D-mannuronic acid in the sample is 98.07% by above method, indicating that the alginate oligosaccharide is mainly composed of mannuronic acid.

4 Structure Identification of the Oxidative Product of the Alginate Oligosaccharide The structure of the oligosaccharide oxidative product fraction obtained from the preparation of the oxidative product of the alginate oligosaccharide is identified. The oxidative product is confirmed to be a derivative of the alginate oligosaccharide composed of β-D-mannuronic acid linked by 1,4 glycosidic bonds, in which the reduced terminal in position 1 is carboxyl radical. The structural formula is:

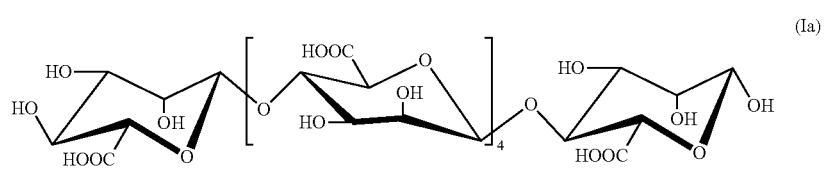

(Ia)

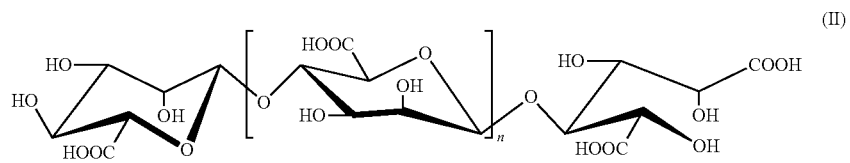

(II)

wherein, n represents a integer of 0 or 1 to 19.

Component 6 is taken as an example to illustrate the structure analysis of above oligosaccharide oxidative product.

4.1 Ultraviolet Absorption Spectrogram

An appropriate oxidative product is diluted to a certain concentration with distilled water, and scanned with Shimdzu UV-260 UV spectrophotometer (190 nm~700 nm) at full wavelength. It is found that no specific absorption peak appeared in ultraviolet and visible light region.

4.2 Infrared Spectroscopy Analysis

Infrared spectrum of the oxidative product of the alginate oligosaccharide is determined by NICOLE NEXUS-470 intelligent infrared spectrometer. The results are shown in table 4.

TABLE 4

IR spectrum of the oxidative product of the alginate oligosaccharide

| Absorption peak (cm$^{-1}$) | Type of vibration | Group | Intensity |
|---|---|---|---|
| 3400.56 | $\upsilon_{OH}$ | —OH | s |
| 3219.02 | $\upsilon_{OH}$ | —OH | s |
|  | $\upsilon_{CH}$ | —COOH |  |
| 2924.65 | $\upsilon_{OH}$ | —COOH | m |
| 1599.76 | $\upsilon_{C=O}$ | —COOH | s |
| 1405.95 | $\upsilon_{C-O}$ | —COOH | s |
| 1296.26 | $\delta_{O-H}$ | —OH | m |
| 1037.84 | $\upsilon_{as}$(C—O—C) | anhydro ether | m |
| 817.14 | $\upsilon_{as}$ (sugar ring) | mannuronic acid cyclic skeleton | m |
| 669.80 | $\gamma_{OH}$ | —OH | m |

4.3 $^1$H-NMR Analysis $^1$H-NMR and $^{13}$C-NMR of the oxidative product are obtained by Bruker Auance DPX-300 NMR spectrometer. As seen from $^1$H-NMR spectrum, it is mainly composed of the signals of six hydrogen atoms in β-D-mannuronic acid. After coupling pattern of each signal is assigned, it is found that the oxidative product of the alginate oligosaccharide is mainly composed of mannuronic acid. If the reduced terminal in position 1 is aldehyde group, chemical shifts of H-1 α and β should be 5.11 ppm and 4.81 ppm, respectively. Since the reduced terminal in position 1 of the alginate oligosaccharide is oxidized to carboxyl from aldehyde group, H-1 disappeared, thus signals at 5.11 ppm and 4.81 ppm disappeared. As seen from $^{13}$C-NMR spectrum, it is mainly composed of the signals of six carbon atoms in β-D-mannuronic acid. After coupling pattern of each signal is assigned, it is found that intermediate molecule is mainly composed of mannuronic acid. Compared with the spectrum of intermediate, the signal of the reduced terminal C-1 of mannuronic acid (94 ppm) disappears. The signal of the reduced terminal C-1 (175.81 ppm) is shifted towards low field. The reason is that the reduced terminal in position 1 of the alginate oligosaccharide is oxidated to carboxyl from aldehyde group, thus chemical shift of C-1 is changed from 94 ppm of aldehyde group to 175.81 ppm of carboxyl.

4.4 MS Analysis

Figure 4:
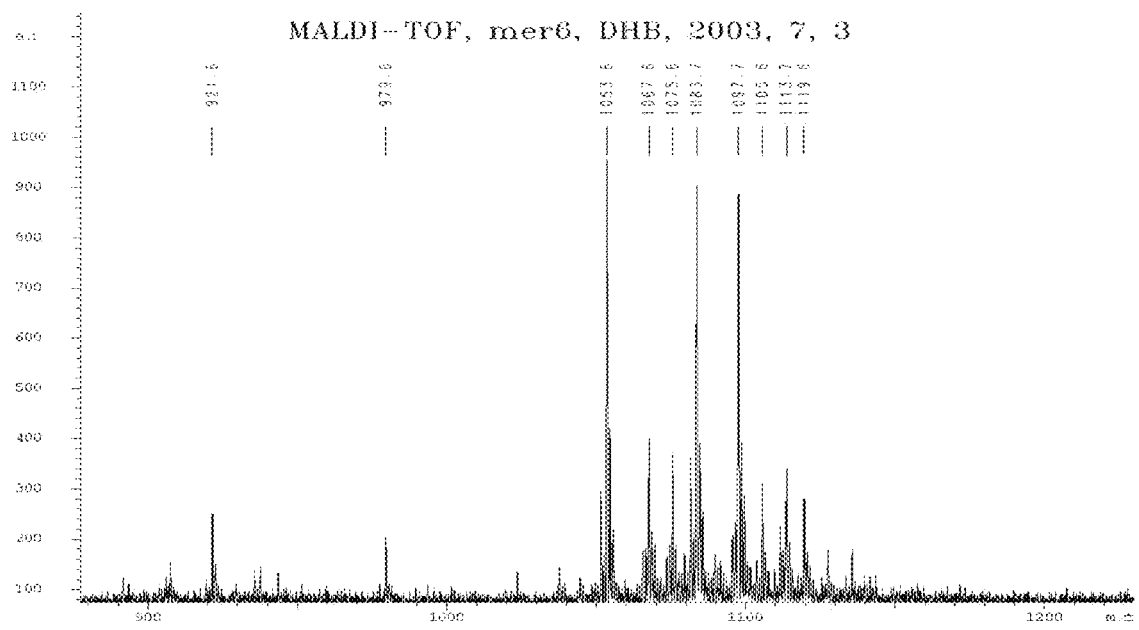
FIG. 4 shows the MALDI-TOF spectrum of the oxidative product of the alginate oligosaccharide (Posotive mode).

MS analysis is performed with BIFLEX III type MALDI-TOF mass spectrometer (Bruker Daltonics Co.). The results are shown in FIG. 4. As seen from FIG. 4, the peak of mz 1113.7 is [M+Na]$^{+1}$; mz 1113.7 is [M–O+Na]$^{+1}$; mz 1083.7 is [M-CH$_2$O+Na]$^{+1}$; mz 1067.6 is [M-CH$_2$O—O+Na]$^{+1}$; mz 1053.6 is [M-2(CH$_2$O)+Na]$^{+1}$; mz 979.6 is [M-3(CH$_2$O)—CO$_2$+Na]$^{+1}$; mz 921.6 is [M-4(CH$_2$O)—CO$_2$—CO+Na]$^{+1}$. MS analysis of the oxidative product of the alginate oligosaccharide is shown in table 5.

TABLE 5

MS analysis of the oxidative product of the alginate oligosaccharide

| Fragment ions | m/z |
|---|---|
| [M + Na]$^{+1}$ | 1113.7 |
| [M-O + Na]$^{+1}$ | 1097.7 |
| [M-CH$_2$O + Na]$^{+1}$ | 1083.7 |
| [M-O—CH$_2$O + Na]$^{+1}$ | 1067.6 |
| [M-2 (CH$_2$O) + Na]$^{+1}$ | 1053.6 |
| [M-3 (CH$_2$O)—CO$_2$ + Na]$^{+1}$ | 979.6 |
| [M-4 (CH$_2$O)—CO$_2$—CO + Na]$^{+1}$ | 921.6 |

In MALDI-TOF spectrum of the oxidative product of the alginate oligosaccharide, the peak of mz 1113.7 is [M+Na]$^{+1}$, indicating that molecular weight of the oxidative product is 1090.7. As the molecular weight increased sixteen compared with that of acid hydrolyzed alginate oligosaccharide (M=1075), that is, the molecule increased an oxygen atom, it is considered that the alginate oligosaccharide is oxidated during the preparation.

According to above analysis results, the structure of the oxidative product of the alginate oligosaccharide is the formula (IIa):

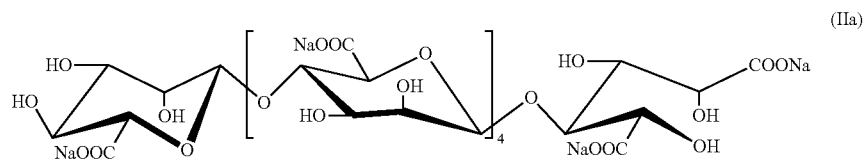

(IIa)

5 Evaluation of Oligomannurarates on Alzheimer's Disease (AD)

The 6-mer separated with Bio-Gel-P6 column is used as an example to show their activity in the following experiments.

5.1 Effects of 6-Mer on AD Mice Induced by $A\beta_{1-40}$

Male Balb/c mice (18-22 g, purchased from Laboratory Centre of Shandong University) are randomly assigned to six groups as follows: 6-mer-treated groups (administered orally for 7 consecutive days at doses of 15, 30 and 60 mg/kg daily prior to $A\beta_{1-40}$ injection), Huperzine A-treated (HBY) group (administered orally with HBY at a dose of 0.2 mg/kg once a day), $A\beta_{1-40}$-injected group (model group, only administered with saline daily), and vehicle group (control group, only administered with saline daily). On day 8, mice are injected with aged $A\beta_{1-40}$ except the vehicle group as the method of reference (Jhoo J H at al, β-amyloid (1-42)-induced learning and memory deficits in mice: involvement of oxidative burdens in the hippocampus and cerebral cortex. Behavioural Brain Research (2004) 155: 185-196) to induce the AD model. Following surgery, mice are further treated with drugs or saline. The effects of 6-mer on Aβ-induced AD model are evaluated with Morris water maze task and step-through test. MDA, superoxide dismutase (SOD), glutathione peroxidase (GSH-Px), $Na^+$, $K^+$-ATPase, AchE and CHAT activities in the brain regions are determined using the respective kits (Nanjing Jiancheng Bioengineering Institute, Nanjing, PR China).

Morris water maze test is conducted in 17 days post drug administration. The results of acquisition trials showed that Aβ-treated mice displayed longer escape latency, comparable with the controls. However, this increased escape latency is shortened in a dose-dependent manner by 6-mer (table 6). In a spatial probe trial (table 7), mice in the Aβ-treated group exhibited lower latency bias than the control mice (P<0.05), and the latency bias of mice is elevated significantly after administration of 6-mer or HBY, compared with that of the Aβ-treated group (P<0.05). HBY, a selective acetylcholinesterase inhibitor, is less potent than 6-mer both in terms of acquisition and spatial probe trials.

Figure 5:
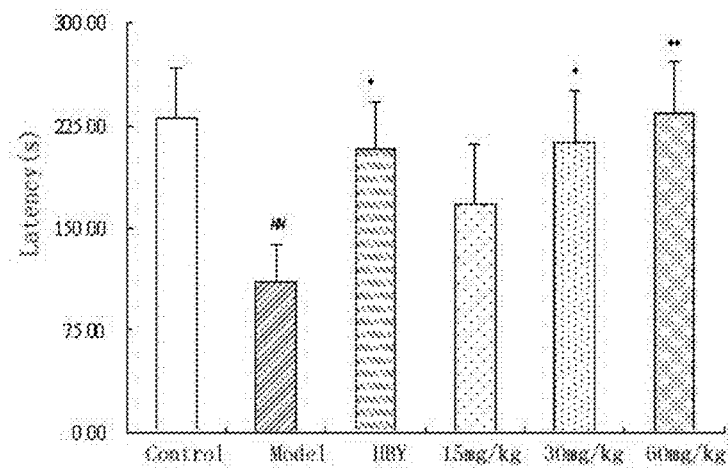
FIG. 5 shows the effect of the alginate oligosaccharide on the latency of AD mice induced by $A\beta_{1-40}$ tested with Morris water maze.
Figure 6:
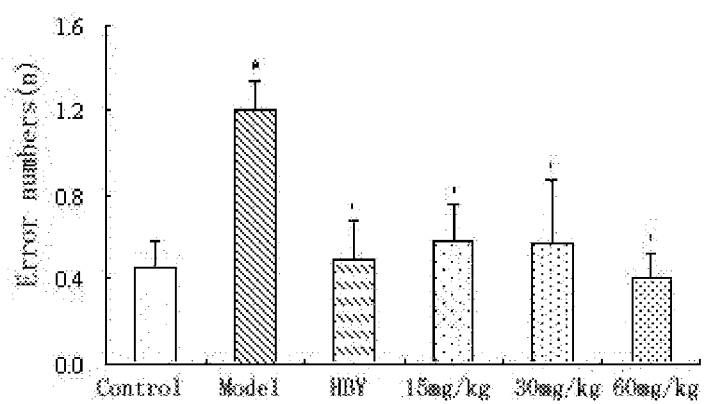
FIG. 6 shows the effect of the alginate oligosaccharide on the error numbers of AD mice induced by $A\beta_{1-40}$ tested with Morris water maze.

Three days after the Morris water maze test, mice are further trained for step-through passive avoidance task. The results are shown in FIGS. 5 and 6. Each group has 8 animals. The data are presented as mean±SE. The symbol # means significantly different compared with control group (P<0.05). * means significantly different compared with model group (P<0.05). The step-through latency is prolonged (FIG. 5), and the number of errors is significantly reduced in 6-mer-treated group in a dose-dependent fashion (FIG. 6), compared with those of the $A\beta_{1-40}$-treated group, indicating that 6-mer markedly and dose-dependently improves $A\beta_{1-40}$-induced amnesia. Moreover, HBY is also less potent than 6-mer, both in terms of learning and memory tasks.

TABLE 6

Effects of 6-mer on escape latency of AD mice induced by $A\beta_{1-40}$ tested with Morris water maze ($\bar{x} \pm SE$)

| Group | Dose (mg/kg) | n | 1st day | 2nd day | 3rd day |
|---|---|---|---|---|---|
| Control | — | 12 | 49.40 ± 8.39 | 54.30 ± 11.39 | 42.80 ± 10.04 |
| Model | — | 14 | 87.20 ± 7.58## | 93.46 ± 8.67# | 97.31 ± 8.65## |
| 6-Mer | 15 | 14 | 90.07 ± 10.71 | 83.29 ± 9.53 | 72.83 ± 12.50 |
|  | 30 | 14 | 77.71 ± 8.69 | 71.69 ± 10.11 | 68.45 ± 14.46 |
|  | 60 | 13 | 56.92 ± 9.92* | 63.57 ± 10.54* | 62.50 ± 13.10* |
| HBY | 0.2 | 14 | 76.29 ± 9.74 | 64.58 ± 10.36* | 63.83 ± 10.12* | p < 0.05,
p < 0.01 vs control;
*p < 0.05 vs model

TABLE 7

Effects of 6-mer on the probe trial of AD mice induced by $A\beta_{1-40}$ tested with Morris water maze ($\bar{x} \pm SE$)

| Group | Dose (mg/kg) | n | Latency bias(%) |
|---|---|---|---|
| Control | — | 12 | 29.48 ± 5.47 |
| Model | — | 14 | 11.83 ± 3.33# |
| 6-Mer | 15 | 14 | 19.67 ± 5.15 |
|  | 30 | 14 | 22.99 ± 5.79 |
|  | 60 | 13 | 28.44 ± 6.08* |
| HBY | 0.2 | 14 | 22.18 ± 5.93 |

P < 0.05 vs control;
*P < 0.05 vs model

Following the Step-through test, rats are decapitated. Cerebral cortex and hippocampus are dissected, and stored at −80° C. until use. MDA, SOD, GSH-PX, $Na^+$, $K^+$-ATPase, AchE and CHAT activities in the brain regions are determined using the respective kits.

(1) Effects of 6-Mer on the ChAT Activity of AD Mice

The ChAT activity in cerebral cortex is markedly decreased after treatment with Aβ, as compared to control group (p<0.05). However its activity is increased after the treatment of 6-mer and HBY, with 30 and 60 mg/kg of 6-mer and HBY have the significantly difference (table 8).

TABLE 8

Effects of 6-mer on the cerebral cortex ChAT activity of $A\beta_{1-40}$-induced AD mice (n = 10, $\bar{x} \pm SE$)

| Group | Dose (mg/kg) | ChAT activity (pmol/mg prot./min) |
|---|---|---|
| Control | — | 92.17 ± 2.95 |
| Model | — | 77.26 ± 4.9# |
| 6-Mer | 15 | 90.94 ± 3.77 |
|  | 30 | 99.98 ± 5.07** |
|  | 60 | 94.69 ± 5.83* |
| HBY | 0.2 | 100.70 ± 5.99** | p < 0.05 vs control;
*P < 0.05,
**P < 0.01 vs model (2) Effects of 6-Mer on the SOD Activity of AD Mice The SOD activity in brain is decreased after treatment with Aβ, but has no statistically significance as compared with control group. Its activity is increased both in cerebral cortex and hippocampus after the treatment of 6-mer at dosage of 60 mg/kg, indicating 6-mer has the antioxidant activity (table 9).

TABLE 9

Effects of 6-mer on the brain SOD activity of $A\beta_{1-40}$-induced AD mice (n = 10, $\bar{x} \pm SE$)

| | | SOD activity (NU/mg prot) | |
|---|---|---|---|
| Group | Dose (mg/kg) | cerebral cortex | hippocampus |
| Control | — | 53.48 ± 1.56 | 66.35 ± 4.74 |
| Model | — | 49.99 ± 2.41 | 62.24 ± 4.16 |
| 6-Mer | 15 | 49.35 ± 2.27 | 69.76 ± 6.12 |
| | 30 | 51.84 ± 2.07 | 61.72 ± 4.27 |
| | 60 | 57.50 ± 2.51* | 79.97 ± 7.34* |
| HBY | 0.2 | 48.95 ± 2.13 | 69.91 ± 6.51 |

*P < 0.05 vs model (3) Effects of 6-Mer on the MDA Content of AD Mice

The MDA content in brain has no statistically significance as compared with control group. Its content is decreased both in cerebral cortex and hippocampus after the treatment of 6-mer at dosage of 30 and 60 mg/kg, indicating 6-mer has the ability of clearance of free radicals (table 10).

TABLE 10

Effects of 6-mer on the brain MDA content of $A\beta_{1-40}$-induced AD mice (n = 10, $\bar{x} \pm SE$)

| | | MDA content (nmol/ml) | |
|---|---|---|---|
| Group | Dose (mg/kg) | cerebral cortex | hippocampus |
| Control | — | 2.61 ± 10.22 | 4.75 ± 0.66 |
| Model | — | 2.18 ± 0.23 | 5.17 ± 0.47 |
| 6-mer | 15 | 1.79 ± 0.15 | 4.28 ± 0.82 |
| | 30 | 1.87 ± 0.18 | 2.48 ± 0.43** |
| | 60 | 1.47 ± 0.11** | 2.18 ± 0.43** |
| HBY | 0.2 | 1.61 ± 0.13* | 2.26 ± 0.39** |

*P < 0.05,
**P < 0.01 vs model (4) Effects of 6-Mer on the GSH-PX Activity of AD Mice The GSH-PX activity in brain is decreased after usage of $A\beta$ with significant difference to control group in hippocampus (p<0.05). Its activity is increased in cerebral cortex after the treatment of 6-mer at dosage of 60 mg/kg (p<0.05, table 11).

TABLE 11

Effects of 6-mer on the brain GSH-PX activity of $A\beta_{1-40}$-induced AD mice (n = 10, $\bar{x} \pm SE$)

| | | GSH-PX (U/mg prot) | |
|---|---|---|---|
| Group | Dose (mg/kg) | cerebral cortex | hippocampus |
| Control | — | 7.81 ± 1.20 | 5.39 ± 0.67 |
| Model | — | 6.43 ± 1.56 | 3.13 ± 0.58# |
| 6-Mer | 15 | 8.53 ± 0.86 | 4.13 ± 0.58 |
| | 30 | 7.12 ± 1.10 | 4.25 ± 0.54 |
| | 60 | 10.75 ± 1.80* | 4.81 ± 0.95 |
| HBY | 0.2 | 8.85 ± 1.33 | 5.29 ± 0.99* |

P < 0.05 vs control;
*P < 0.05 vs model (5) Effects of 6-Mer on the Na+, K+-ATPase Activity of AD Mice The Na+, K+-ATPase activity in brain is significantly decreased after treatment with $A\beta$ as compared with control group, while its activity is markedly increased after the treatment of 6-mer (P<0.05, table 12).

TABLE 12

Effects of 6-mer on the brain Na+, K+-ATPase activity of $A\beta_{1-40}$-induced AD mice (n = 10, $\bar{x} \pm SE$)

| | | ATPase activity (μmol Pi/mg prot./hour) | |
|---|---|---|---|
| Group | Dose (mg/kg) | cerebral cortex | hippocampus |
| Control | — | 1.06 ± 0.05 | 2.65 ± 0.38 |
| Model | — | 0.89 ± 0.06# | 1.62 ± 0.17# |
| 6-Mer | 15 | 1.08 ± 0.06* | 2.10 ± 0.29 |
| | 30 | 1.09 ± 0.08* | 2.07 ± 0.23 |
| | 60 | 1.08 ± 0.05* | 2.52 ± 0.25* |
| HBY | 0.2 | 0.91 ± 0.05 | 2.35 ± 0.43 |

P < 0.05 vs control;
*P < 0.05 vs model 5.2 Protective Effects of 6-Mer on Neurons Impaired by $A\beta$ in Vitro The cerebral cortex neurons of rat are cultured as the method of reference (Banker G A, et al, Rat hippocampal neurons in dispersed cell culture. Brain Res, 1977, 126:397-425). The cells cultured for 1 week are used in this experiment. Briefly, primary cultured neurons cultured for 7 days are seeded in 96-well plates at a density of $1\times10^5$ cells per well, and grown in Dulbecco's modified Eagle's medium (DMEM, Hyclone, Logan, Utah, U.S.A) containing 10% fetal bovine serum (FBS, Hyclone, Logan, Utah, U.S.A). The day after plating, cells are pretreated with varying concentrations of 6-mer (final concentration of 0, 10, 50, 100 μg/ml) for 24 h, followed by the addition of aged $A\beta_{25-35}$ (Firstly resolved in distilled water with concentration of 1 mg/ml, then stayed at 37° C. for 7 days to get aged $A\beta_{25-35}$) with final concentration of 30 μM. After 24 h at 37° C., 10 μl MTT with concentration of 5 mg/ml are added. After 4 hour at 37° C., the supernatant are removed and 150 μl DMSO are added. Then the absorbance at 570 nm (630 nm as reference) is recorded with an ELISA reader (Rainbow, TECAN, Austria).

The results showed that the survival of the cells are significantly reduced after treatment with aged $A\beta_{25-35}$ (the survived cells reduced to 54.5±8.9%, P<0.001 compared to control). 6-mer at dosage of 10, 50, 100 μg/ml could increase the survived cells impaired by $A\beta_{25-35}$ in a dose-dependent manner (the survived cells are 72.0±11.2%, 77.1±8.1% and 82.3±11.6% respectively).

Figure 7:
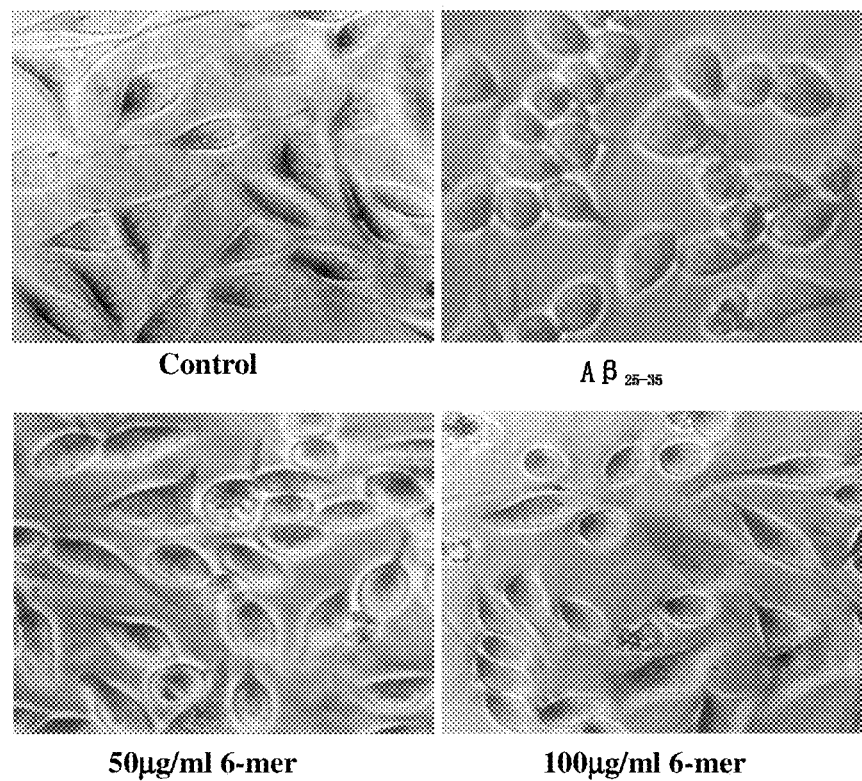
FIG. 7 shows the protective effects of the alginate oligosaccharide on SH—SY5Y cells impaired by $A\beta_{25-35}$.
Figure 8:
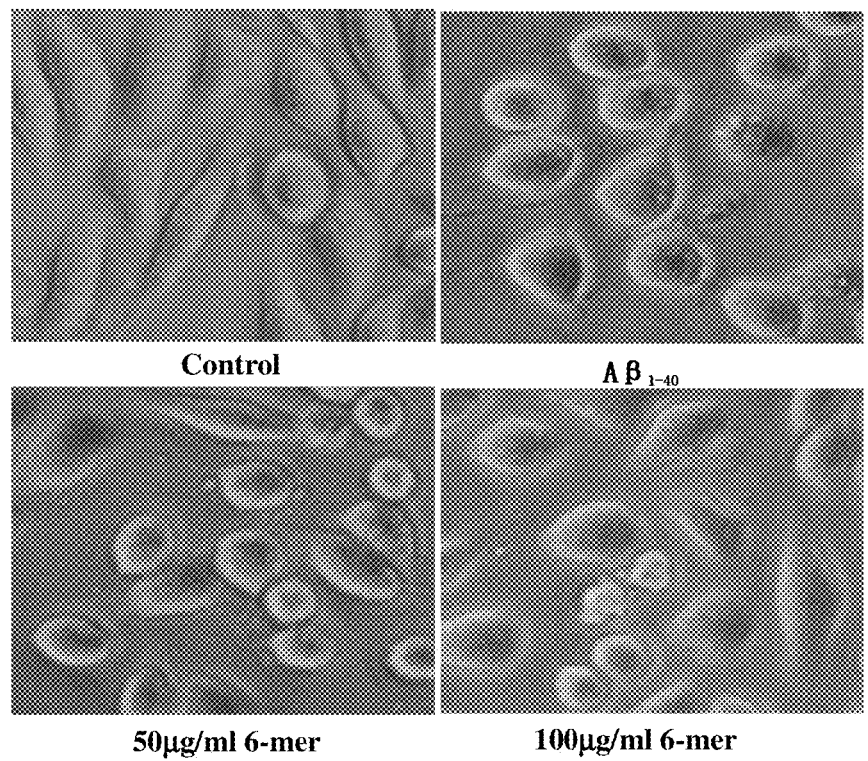
FIG. 8 shows the protective effects of the alginate oligosaccharide on SH—SY5Y cells impaired by $A\beta_{1-40}$.

6-mer has the similar protective effects on neuron cell line SH—SY5Y impaired with aged $A\beta_{25-35}$ and $A\beta_{1-40}$ (FIG. 7,8). 30 μM Aged $A\beta_{25-35}$ and 2 μM $A\beta_{1-40}$ could impair the cells with the survived cells of 73.3±9.4% and 64.1±2.5% when treated for 48 h. 6-mer at dosage of 50, 100 μg/ml could inhibit the neurotoxicity of $A\beta$.

The above experiments revealed that 6-mer could shorten the escape latency and increase the numbers of crossing the original plate and shorten the time of arriving the original plate on AD mice induced with $A\beta_{1-40}$, implying its behavioural improvement activity in $A\beta$-treated mice. This in vivo result as well as the in vitro protective effects on primary and neuron cell lines supported that 6-mer has the anti-AD activity.

6 Action Mechanism Study of 6-Mer on AD

6.1 Effects of 6-Mer on the Apoptosis of Cell Line SH—SY5Y Induced by $A\beta_{25-35}$ SH—SY5Y cells are seeded in 6-well plates at a density of $2\times10^5$ cells per well, and grown in DMEM medium containing 10% FBS. The day after plating, cells are pretreated with varying concentrations (0, 50, 100 µg/ml) of 6-mer for 24 h, followed by the addition of 30 µM aged $A\beta_{25-35}$. After 48 h at 37° C., cells are collected, washed, and stained with propidium iodide (5 µg/ml containing 100 U/ml RNase). Then the cells ($1\times10^4$) are used for cell-cycle analysis by Flow cytometry.

The results found that SH—SY5Y cells treated with 30 µM aged $A\beta_{25-35}$ show 24.8±1.9% hypodiploid cells. However, pretreatment with 50 and 100 µg/ml 6-mer for 24 h suppressed apoptosis induced by aged $A\beta_{25-35}$ for 24 h, and the observed percentages of hypodiploid cells are 10.2±1.3% and 5.1±0.7%, respectively.

Further study revealed that 6-mer also significantly arrested apoptotic cascade by reversing overload of intracellular calcium ion and ROS accumulation, thus up-regulating Bcl-2 and down-regulating P53 and Caspase-3 expression induced by Aβ. All these factors contribute to the therapeutic potential of 6-mer in the treatment of AD.

6.2 Molecular Mechanism of 6-Mer on Anti-Neuron Toxicity of Aβ

(1) Effects of 6-Mer on the Fibril Formation of $A\beta_{1-40}$

The Th-T fluorometric assay is used to measure β-sheet formation of Aβ fibril. To evaluate the effects of 6-mer on fibrillogenesis, 1.0 mg/ml monomeric $A\beta_{1-40}$ is incubated alone or with 6-mer (final concentration of 0, 10, 50, 100 µg/ml) or heparin or with the concomitant presence of 6-mer and heparin at 37° C. for 24 h and 48 h in 150 mM phosphate buffer (pH 7.4). After incubation, 10 µl of above solution is added to Th-T at a final concentration of 3.0 µM in a volume of 0.3 ml of 50 mM phosphate buffer (pH 6.0). Fluorescence is monitored at Em=450 nm and Ex=480 nm, using Jasco FP6200 fluorescence spectrophotometer. The fluorescence of each sample is corrected by subtracting from the background fluorescence of 3.0 µM Th-T. Data from three identical samples in separate experiments are averaged to provide the final values.

Figure 9:
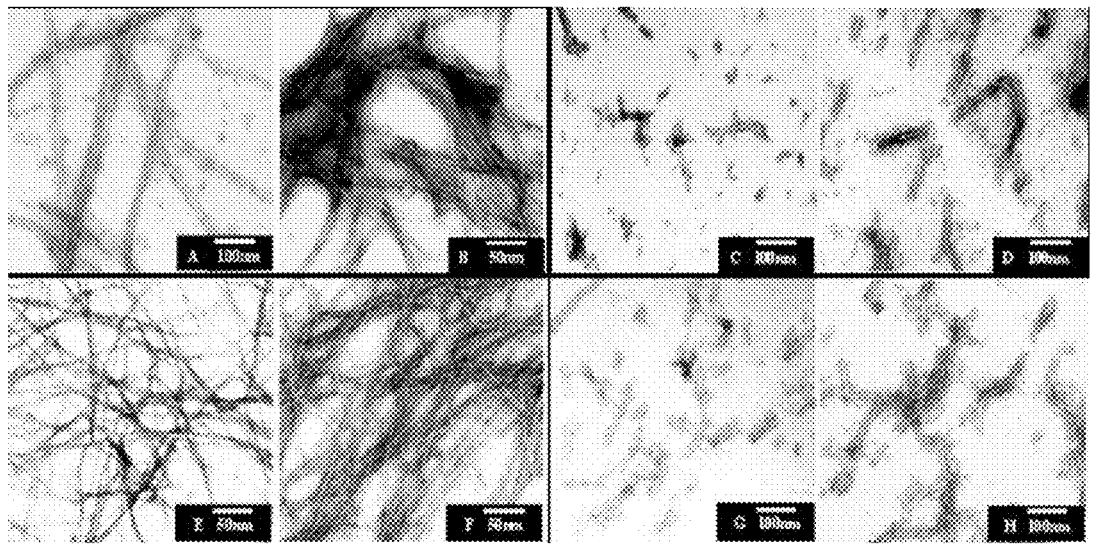
FIG. 9 shows the inhibitory effects of the alginate oligosaccharide on normal and heparin-induced fibril formation of $A\beta_{1-40}$.

The results show that Th-T fluorescence intensity increased in the presence of $A\beta_{1-40}$. However, 6-mer (at dosage of 10, 50, 100 µg/ml) decreases Th-T fluorescence intensity significantly 10.46±0.94, 9.18±1.32 and 7.81±1.38 (p<0.05, 0.05 and 0.001). The same effects of 6-mer on the fibril formation of $A\beta_{1-40}$ are studied with TEM (JEM-1200EX) (FIG. 9). A is the photo of $A\beta_{1-40}$ alone incubated for 24 h; B is the mixture of $A\beta_{1-40}$ and heparin incubated for 24 h; C is the mixture of $A\beta_{1-40}$ and 6-mer incubated for 24 h; D is the mixture of $A\beta_{1-40}$, heparin and 6-mer incubated for 24 h; F is $A\beta_{1-40}$ alone incubated for 48 h; G is the mixture of $A\beta_{1-40}$ and 6-mer incubated for 24 h; H is the mixture of $A\beta_{1-40}$, heparin and 6-mer incubated for 24 h. These findings indicate that 6-mer suppresses both fibrillogenesis of $A\beta_{1-40}$ alone and is facilitated by heparin.

(2) Effects of 6-Mer on the Destability of $A\beta_{1-40}$ Fibril.

Figure 10:
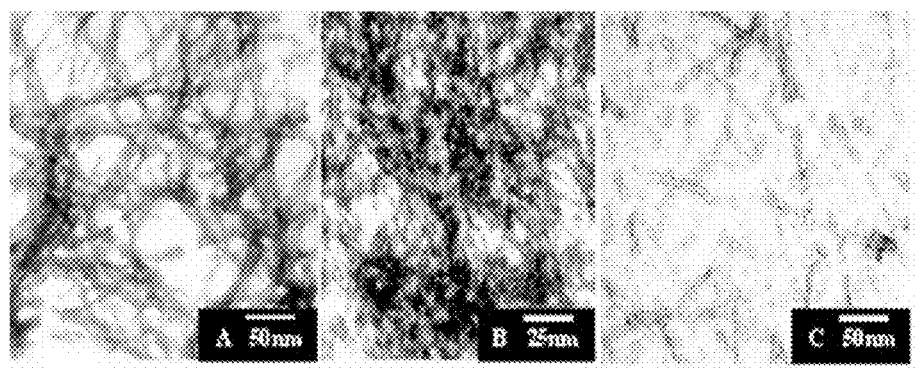
FIG. 10 shows the destabilized effects of the alginate oligosaccharide on fibril $A\beta_{1-40}$.

Distilled water-resolved $A\beta_{1-40}$ is initially allowed to assemble for 1 week, after which it is exposed to 6-mer or heparin for 3 days. TEM reveals that $A\beta_{1-40}$ alone leads to the formation of long, twisted fibers following 7 days incubation at 37° C. (FIG. 10A). In the presence of heparin for an additional 24 h, the long, twisted fibers become much denser and longer compared to those formed in the absence of heparin (FIG. 10B). Notably, in the presence of 6-mer, the long and aggregated Aβ fibers are turned into small irregular short fibers (FIG. 10C). These findings suggest that 6-mer is capable of reversing preformed Aβ fibril, highlighting the destabilizing action of 6-mer on preformed Aβ fibril and thus potentially therapeutic intervention.

(3) Effects of 6-Mer on the β-Sheet Formation of $A\beta_{1-40}$

Figure 11:
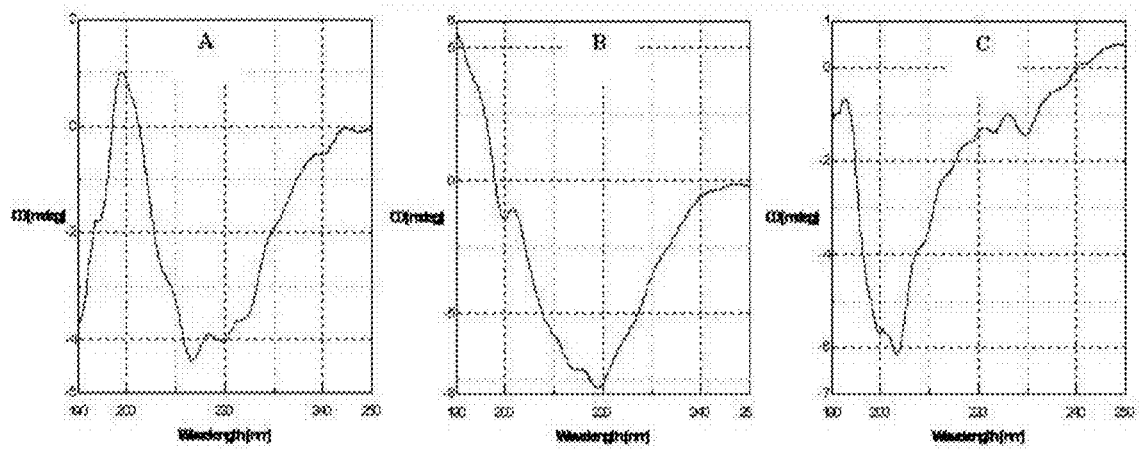
FIG. 11 shows the effects of the alginate oligosaccharide on the conformation of soluted 250 μg/ml $A\beta_{1-40}$.

Fibrillogenesis strictly depends on the structural transition of Aβ peptide from α-helix or random coils to an organized β-sheet conformation. CD spectra (J-500A, JASCO, Japan) of monomeric $A\beta_{1-40}$ (250 µg/ml in TBS (100 mM Tris, 50 mM NaCl, pH7.4)) incubated for 12 h is mainly characterized by β-sheet secondary structure (FIG. 11A). The simultaneous exposure of monomeric $A\beta_{1-40}$ to 6-mer (100 µg/ml) for 12 h prevents the β-sheet formation (FIG. 11C). However, heparin significantly accelerates the conformational transition to β-sheet structure (FIG. 11A).

(4) Interaction Between 6-Mer and Aβ

SPR technique (BIAcore X, Uppsala, Sweden) is used to characterize the interaction of 6-mer and Aβ. Different degree of aged $A\beta_{1-40}$ (aged for 0, 0.5, 1, 2, 4, 6 days at 37° C.) in a series concentrations are flowed through the 6-mer-immobilized sensor chip. The flow rate is 5 µl/min, and the injection volume is 10 µl. The binding sensorgram is recorded and the sensor chip is regenerated with 2M NaCl.

The results showed that different degrees of aged $A\beta_{1-40}$ all could bind to 6-mer. The binding affinity is weak of fresh $A\beta_{1-40}$ with $K_D$ value of 6.85 E-07 M. The binding affinity increased with aged degree ($K_D$ values are 1.07 E-07, 9.06 E-08, 5.43 E-08, 2.15 E-08, 1.45 E-08 M respectively), almost stable after aged for 2 days.

Further studies reveal that 6-mer bind to the full length Aβ through His13~Lys16, while Ser26~Lys28 is the binding site of 6-mer on $A\beta_{25-35}$. The binding of 6-mer with fresh Aβ might contributed to its inhibition on fibrillogenesis of Aβ. The binding of 6-mer with aged Aβ might contributes to its disassemble ability on fibril Aβ.

The above studies reveal that the molecular mechanisms are attributed to the fact that 6-mer both hinder the whole fibrillogenetic process and particularly disassemble the preformed Aβ fibril via binding HHQK epitopes on Aβ. These results indicate that 6-mer, acting as a full Aβ cascade antagonist, is a potential preventive and therapeutic candidate for AD, which provides the proof of principle for a new strategy for cure of AD.

7 Study of 6-Mer on Diabetes Models

7.1 Protective effects of 6-mer on pancreatic beta-cells impaired by amylin

The pancreatic beta-cells cell line NIT is cultured with DMEM containing 10% FBS. The cells are planted in 96-well plate in density of $1\times10^4$ cells/well. The day after plating, cells are pretreated with varying concentrations of 6-mer (final concentration of 0, 10, 50, 100 µg/ml) for 24 h, followed by the addition of aged amylin with final concentration of 30 µM. After 48 h at 37° C., 10 µl MTT with concentration of 5 mg/ml are added. After 4 hour at 37° C., the supernatants are removed and 150 µl DMSO are added. Then the absorbance at 570 nm (630 nm as reference) is recorded with an ELISA reader.

Figure 12:
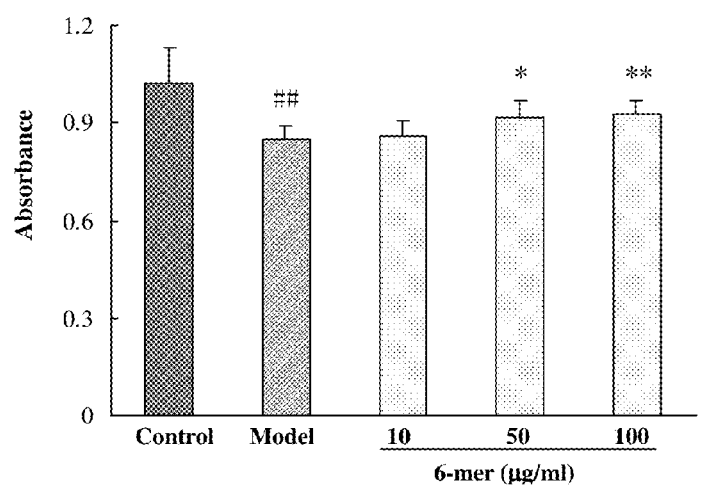
FIG. 12 shows the protective effects of the alginate oligosaccharide on NIT cells impaired by IAAP.
Figure 13:
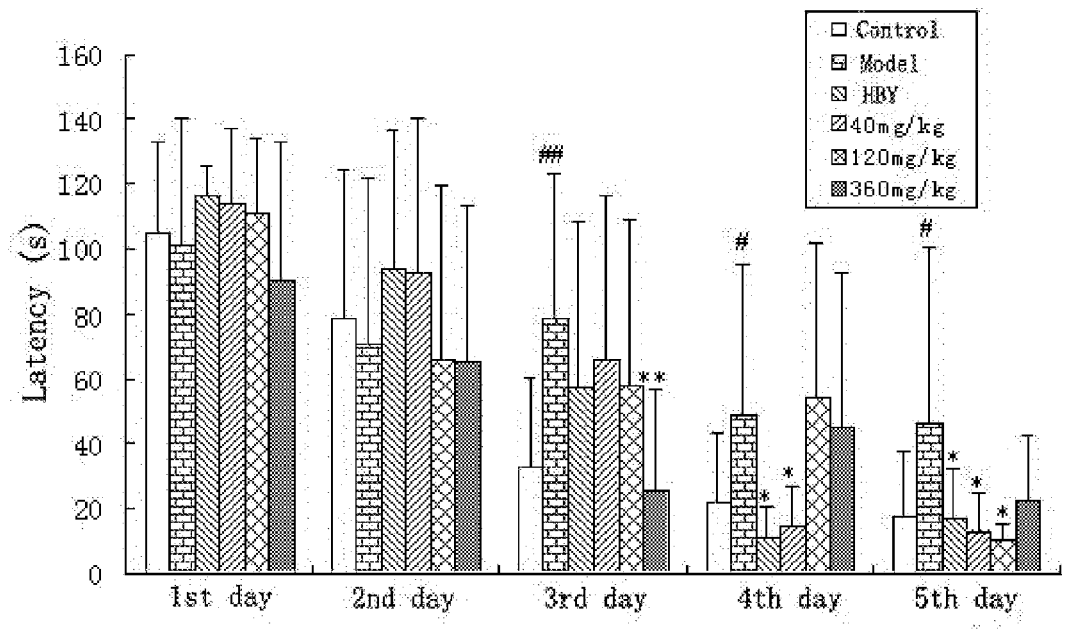
FIG. 13 shows the effect of the mixture of oxidative product of the alginate oligosaccharide on the latency of AD mice induced by $A\beta_{1-40}$ tested with Morris water maze.
Figure 14:
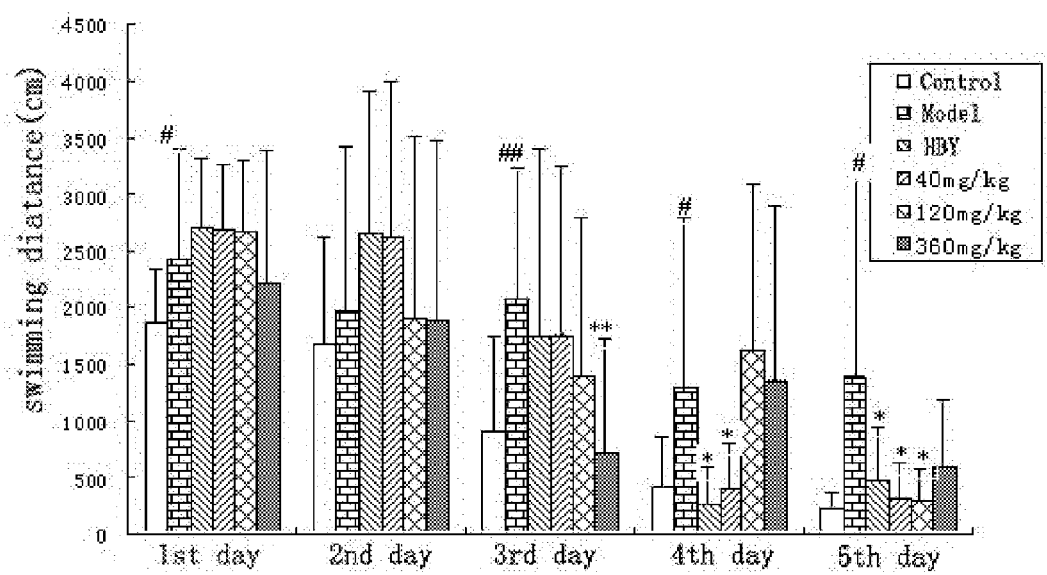
FIG. 14 shows the effect of the mixture of oxidative product of the alginate oligosaccharide on the swimming distance of AD mice induced by $A\beta_{1-40}$ tested with Morris water maze.
Figure 15:
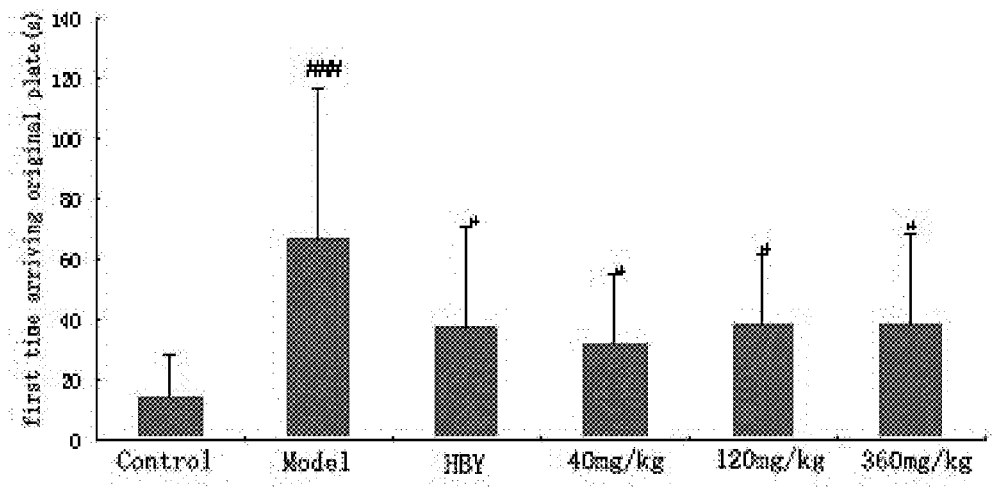
FIG. 15 shows the effect of the mixture of oxidative product of the alginate oligosaccharide on the first time arriving the original plate of AD mice induced by $A\beta_{1-40}$ tested with Morris water maze.
Figure 16:
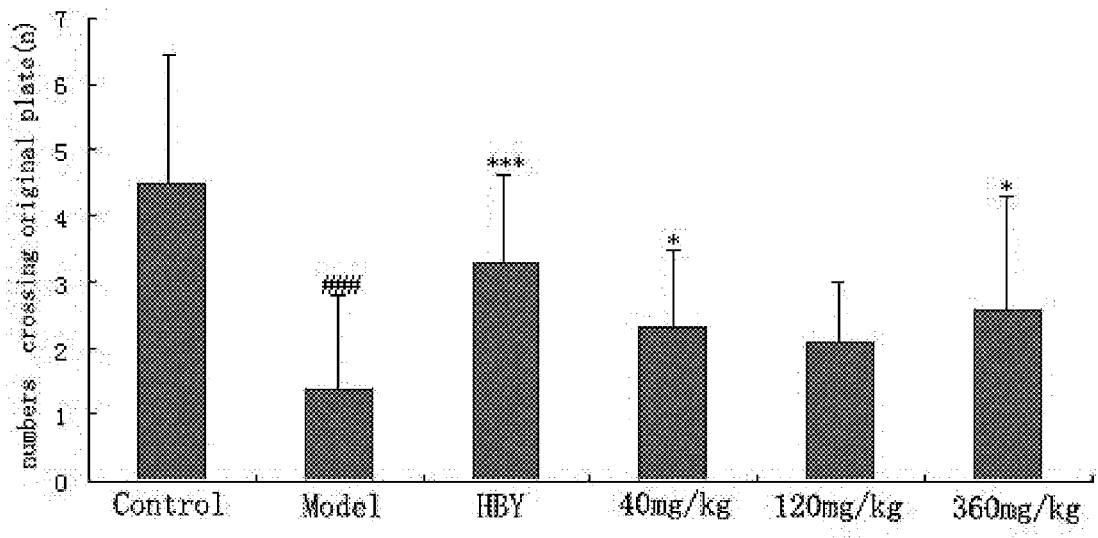
FIG. 16 shows the effect of the mixture of oxidative product of the alginate oligosaccharide on the numbers crossing the original plate of AD mice induced by $A\beta_{1-40}$ tested with Morris water maze.

The results show that 6-mer could increase the survived cells impaired by amylin in a dose-dependent manner (FIG. 12). The data implies that 6-mer has the protective effects on cells impaired with amylin. The repeated wells are 6. The data is shown as mean±SE. ## means significantly different compared with control (p<0.01). * and ** means significantly different compared with model (p<0.05 and p<0.01).

7.2 Effects of 6-Mer on the Diabetic Mice Induced by Streptozotocin (STZ)

Sixty male NIH mice (weighed 18-22 g) are randomly divided to control, model, 50, 150, 450 mg/kg 6-mer and 5 mg/kg dimethyldiguanide groups. The mice are injected intraperitoneally with 150 mg/kg STZ except control group at the 1st day. Then the mice are given accordingly drugs consecutively for 10 days. The blood was taken to detect the glucose concentration after 30 min of final drug administration. The results show that the blood glucose concentration is increased after treatment with STZ. The concentration are lowed when treated with 6-mer. This data indicated that 6-mer have therapeutic activity on STZ-induced diabetic mice (table 13).

TABLE 13

Effects of 6-mer on the blood glucose concentration of diabetic mice induced by STZ ($\bar{x} \pm SD$)

| Group | Dose (mg/kg) | Number | Blood glucose concentration (mg/dL) |
|---|---|---|---|
| Control | — | 10 | 150.6 ± 36.8 |
| Model | — | 10 | 312.4 ± 89.2### |
| 6-mer | 50 | 10 | 219.4 ± 67.8* |
|  | 150 | 10 | 179.6 ± 69.8** |
|  | 450 | 10 | 162.5 ± 3** |
| Dimethyldiguanide | 5 | 10 | 201.6 ± 58.9** |

$p < 0.05$ vs control;
*$P < 0.05$,
**$p < 0.01$ vs model

Figure 17:
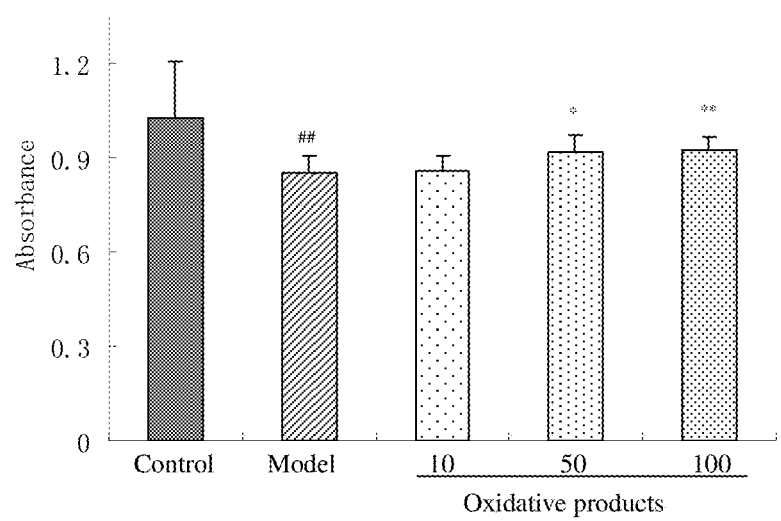
FIG. 17 shows the protective effects of the mixture of oxidative product of the alginate oligosaccharide on NIT cells impaired by IAAP.

The same experiments are conducted with 2-mer to 22-mer alone or their mixture or oxidative products. The results are similar to that of 6-mer to indicate their potential activity on AD and diabetes. FIGS. 13-16 showed the behavioral results of mixture of oxidative products of alginate on AD mice induced by $A\beta_{1-40}$ injected to brain. Each group has 8 animals. The data presented as mean±SE. The symbol # and ## stand for significantly different compared to control group ($p < 0.05$, $p < 0.01$), and * and ** stand for significantly different compared to model group ($p < 0.05$, $p < 0.01$). This data revealed that oligomannurarate could improve the learning and memory ability of AD mice. FIG. 17 showed the protective results of mixture of oxidative products of alginate on cell lines NIT impaired by amylin. Each group has 6 wells. The data presented as mean±SD. The symbol ## stands for significantly different compared to control group ($p < 0.01$), and * and ** stand for significantly different compared to model group ($p < 0.05$, $p < 0.01$). This data revealed that oligomannurarate has potential activity on diabetes.

8 Statistic Analysis

Data are expressed as mean±standard deviation (SD) or standard error (SE), as indicated. Student t-test and analysis of variance (ANOVA) followed by Newman-Keuls post hoc test are performed to assess the differences between the relevant control and each experimental group. Results of water maze training are specifically assessed by mixed design ANOVA. P-values of <0.05 and 0.01 are regarded as statistically significant.

Based on the above results, the pharmaceutical composition containing an effective amount of the mannuronic acid oligosaccharide derivatives and pharmaceutically-acceptable carriers can be easily prepared. The said pharmaceutical composition is any one of a medicament for the prophylaxis and treatment of AD, an amyloid-β protein fibrils forming inhibitor, a medicament for the prophylaxis and treatment of diabetes, an islet amyloid protein fibrils forming inhibitor and a fibrils disaggregating promoter. The invented alginate oligosaccharide has important values in preparing drugs for prophylaxis and treatment of AD and diabetes.

We claim:

1. An alginate oligosaccharide or its derivatives represented by formula (I) or pharmaceutically-acceptable salts thereof, said oligosaccharide is composed of β-D-mannuronic acid linked by 1,4 glycosidic bonds, as shown by the following formula (I):

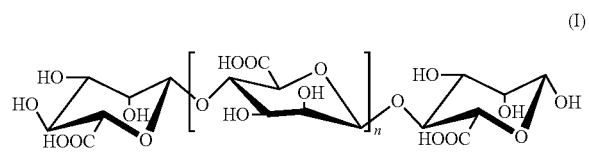

(I)

characterized in that the reduced terminal in position 1 of said alginate oligosaccharide is carboxyl radical, as shown by the following formula (II):

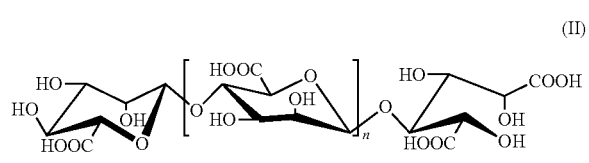

(II)

wherein, n represents a integer of 0 or 1 to 19.

2. A pharmaceutical composition containing an effective amount of the alginate oligosaccharide or its derivatives according to claim 1, and pharmaceutically-acceptable carriers.

3. The pharmaceutical composition according to claim 2, characterized in that the composition is any one of a medicament for the prophylaxis and treatment of AD, an amyloid-β protein fibrils forming inhibitor, a medicament for the prophylaxis and treatment of diabetes, an islet amyloid protein fibrils forming inhibitor and a fibrils disaggregating promoter.

4. Alginate oligosaccharide derivatives or their pharmaceutically-acceptable salts made by the following process:
   an alginate solution is reacted for about 2 to 6 h in an autoclave at pH 2-6 and the temperature of about 100~120° C.,
   adjusted pH to about 7 after the reaction is stopped, and
   an oxidant is added and reacted for 15 min to 2 h at the temperature of 100~120° C.,
   wherein the alginate oligosaccharide derivatives are composed of β-D-mannuronic acid linked by 1,4 glycosidic bonds, wherein the reduced terminal in position 1 is carboxyl radical, as shown by the following formula II:

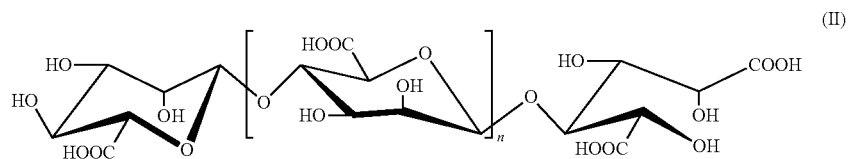
(II)
wherein, n represents 0 or an integer of 1 to 19.
* * * * *